United States Patent [19]

Iinuma

[11] 4,252,125
[45] Feb. 24, 1981

[54] ULTRASONIC DIAGNOSING APPARATUS

[75] Inventor: Kazuhiro Iinuma, Yokohama, Japan

[73] Assignee: Tokyo Shibaura Denki Kabushiki Kaisha, Yokohama, Japan

[21] Appl. No.: 39,596

[22] Filed: May 16, 1979

[30] Foreign Application Priority Data

May 19, 1978 [JP] Japan .................................. 53-58738

[51] Int. Cl.³ .............................................. A61B 10/00
[52] U.S. Cl. ........................................ 128/660; 73/644; 128/661
[58] Field of Search ................... 128/660, 661; 73/644, 73/605, 632

[56] References Cited

U.S. PATENT DOCUMENTS

| 3,990,296 | 11/1976 | Erikson | 128/660 X |
| 4,094,306 | 6/1978 | Kossoff | 128/660 X |
| 4,186,747 | 2/1980 | Iinuma | 128/660 |
| 4,206,763 | 6/1980 | Pedersen | 128/660 |

Primary Examiner—Kyle L. Howell
Attorney, Agent, or Firm—Oblon, Fisher, Spivak, McClelland & Maier

[57] ABSTRACT

At the bottom of a receptacle for medical examinations which is filled with warm water, there is an ultrasonic probe swinging along the bottom face for sector-shaped mechanical scanning and also for electronic scanning in a longitudinal direction at right angles to the mechanical scanning direction. Immersed in the warm water, an ultrasonic-wave transmitting flexible membrane is stretched across the receptacle above the ultrasonic probe. This membrane is provided with a plurality of pores through which the warm water passes. A breast to be examined is pressed against the membrane while it is immersed in the warm water, and a sectional image of the breast is displayed on a display unit by means of the ultrasonic probe.

8 Claims, 4 Drawing Figures

ULTRASONIC DIAGNOSING APPARATUS

This invention relates to an ultrasonic diagnosing apparatus particularly suited for group mastocarcinoma examinations.

Conventional ultrasonic diagnosing apparatus for mastocarcinoma examinations are so constructed that an ultrasonic probe is disposed in a receptacle filled with warm water, ultrasonic waves are applied by means of the ultrasonic probe to a breast immersed in the warm water, and a reflected image is displayed as a sectional view on a display unit. There is, however, a substantial difference among individuals in the size of the breast. Meanwhile, limited is the range of the visual field to secure definite examination by means of the ultrasonic probe or the range of the distance from the probe, so that a highly good-sized breast cannot provide its whole image with high resolution. In an extreme case, the tip of the breast may touch the probe to disturbe the image for such portion.

As another example, there is proposed an apparatus with such construction that the top opening of a receptacle containing an ultrasonic probe therein is sealed with a flexible membrane, the receptacle being filled with warm water. In this case, although a patient undergoes an examination in a prone position so that her breast may touch the flexible membrane, the whole of the breast may not be able to touch the membrane, and it is impossible to obtain a clear ultrasonic image of an untouched portion. Moreover, since a satisfactory ultrasonic image can be obtained only if the surface of the warm water in the receptacle is in touch with the flexible membrane, such condition requires incessant checking, which will be troublesome especially in group examinations.

Accordingly, the object of this invention is to provide an easy-to- operate ultrasonic diagnosing apparatus specially suited for group medical examinations and capable of providing clear sectional images of satisfactory resolution.

According to this invention, there is provided an ultrasonic diagnosing apparatus comprising a receptacle containing a liquid, an ultrasonic-wave transmitting flexible membrane stretched across the receptacle under the surface of the liquid and having a passage portion through which the liquid passes freely, an ultrasonic probe disposed in the liquid in the receptacle, and a means for displaying and recording sectional information on a patient provided by the ultrasonic probe.

This invention can be more fully understood from the following detailed description when taken in conjunction with the accompanying drawings, in which.

Figure 1:
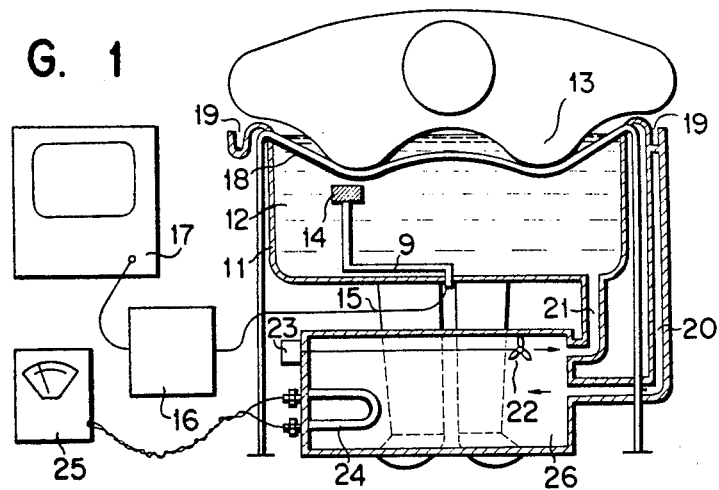
FIG. 1 shows an overall structure of an ultrasonic diagnosing apparatus according to an embodiment of this invention.

Now there will be described in detail an embodiment of this invention with reference to the accompanying drawings. In FIG. 1, a receptacle 11 is filled with a liquid or water 12. Near to the top of the receptacle 11 is provided a flexible membrane 18 to support part (breast) of a patient. The membrane 18 has liquid passage portion consists of notches 28 formed at four corners of the membrane 18. The membrane 18, which may be formed of vinyl, rubber, polyethylene or vinyl chloride, has a property to transmit ultrasonic waves. Further, the membrane 18 may be opaque or transparent for the observation of the state of the liquid 12 in the receptacle 11.

Figure 2:
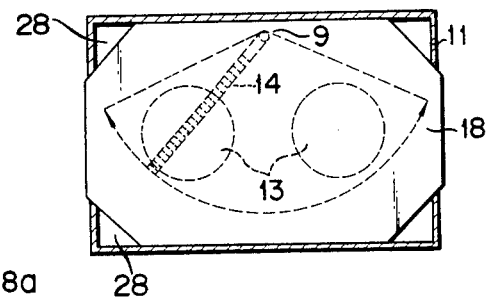
FIG. 2 is a top view of part of a receptacle as shown in FIG. 1.

As shown in FIG. 1, the receptacle 11 is disposed at such a height that the patient in a standing posture may immerse her breast 13 in the liquid 12. An ultrasonic probe 14 has its one end supported by a rotating shaft 9 penetrating through the bottom of the receptacle 11 into the liquid 12. A reflected wave of an ultrasonic wave pulse emitted from the ultrasonic probe 14 in the receptacle 11 to which an output from a pulser (not shown) is applied is again received by the probe 14. The probe 14 is composed of a plurality of ultrasonic transducer elements arranged in a straight line in parallel with the bottom of the receptacle and is scanned in a sector manner as shown in FIG. 2 about an axis 9. Accordingly, a pair of breasts 13 can be examined through only one time of the sector like scanning movement of the probe 14. The reflected signal is sent by means of a cable 15 to a processing circuit 16, where it is processed. Then, a sectional image of the breast 13 is displayed on the screen of a display unit 17. According to the apparatus of this embodiment, the membrane 18 has flexibility, and the breast is allowed to sink to a predetermined depth. Since the membrane 18 can securely transmit ultrasonic waves, the sectional image will not be adversely affected, and the patient will never feel uncomfortable when she immerses her breast in the liquid 12. Moreover, it is essential to keep the water temperature constant in order to harmonize the acoustic impedances among the liquid, membrane and patient and to eliminate the reflection on the skin surface. Provided for this purpose is a temperature control water tank 26 in which a heater 24 is controlled by means of a temperature control device 25 to maintain the temperature of the water in the tank 26 constant. The liquid is introduced into the receptacle 11 through a supply pipe 21 by means of a screw 22 driven by a motor 23, transmitted through the membrane to overflow into a gutter 19, and and then returned to the tank 26 through a return pipe 20.

Figure 3:
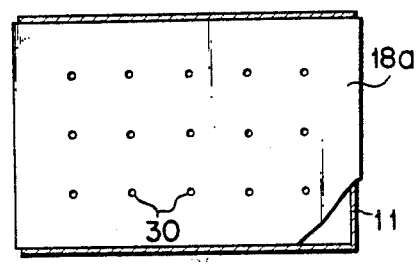
FIG. 3 shows a modification of a flexible membrane as shown in FIG. 1.
Figure 4:
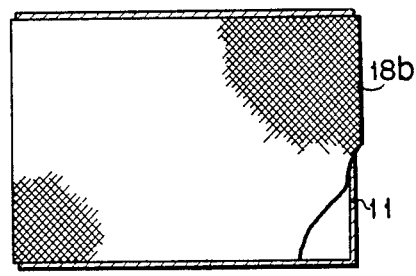
FIG. 4 shows another modification of the flexible membrane.

In the aforementioned embodiment, the membrane 18 used may have a number of pores 30, as shown in FIG. 3. Use of such membrane 18a with the pores 30 facilitates the circulation of the liquid, thus maintaining with ease the liquid at a fixed temperature, e.g. 37° C. Further, by using such membrane 18a, the liquid may conveniently be supplemented so as to maintain the water level constant if it is spilled out of the receptacle. The same such effects may be obtained by using a netlike support 18b as shown in FIG. 4, instead of using the membrane 18 or 18a.

Thus, according to this invention, the patient can enjoy an easy and quick medical examination, so that the apparatus of the invention is specially suited for a group mastocarcinoma examination. In this case, the ultrasonic probe used may be formed of electronic-scanning array transducers. Mechanical scanning in a direction perpendicular to the array of transducers enables recording of solid information in a few seconds.

Furthermore, good-sized breasts may be supported by the membrane, and the depth to which the breast may sink is limited within a fixed range as taken from the ultrasonic probe. Thus, a high-resolution sectional image may be obtained by designing the ultrasonic probe and signal processor so as to provide optimum bearing resolution in accordance with the depth range. Moreover, the liquid lies between the membrane and the breast, so that the acoustic coupling between the probe and the patient can be maintained satisfactorily.

What is claimed is:

1. An ultrasonic diagnosing apparatus comprising:
   a receptacle containing a liquid;
   an ultrasonic-wave transmitting flexible membrane stretched across said receptacle under the surface of the liquid and having a passage portion through which the liquid passes freely;
   an ultrasonic probe disposed in the liquid in said receptacle; and
   a means for displaying and recording sectional information on a patient provided by said ultrasonic probe.

2. An ultrasonic diagnosing apparatus according to claim 1, wherein said liquid passage portion consists of notches formed at the four corners of said membrane.

3. An ultrasonic diagnosing apparatus according to claim 1, wherein said liquid passage portion consists of a number of pores formed in said membrane.

4. An ultrasonic diagnosing apparatus according to claim 1, wherein said membrane is a net.

5. An ultrasonic diagnosing apparatus according to claim 1, wherein the liquid in said receptacle is warm water and including means for compulsively circulating said water through a constant-temperature water bath.

6. An ultrasonic diagnosing apparatus according to claim 1, wherein said membrane is formed of one of vinyl chloride, rubber and polyethylene.

7. An ultrasonic diagnosing apparatus according to claim 1, wherein said ultrasonic probe has its end supported by a rotating shaft penetrating through the bottom of said receptacle, and is formed of a plurality of ultrasonic transducer elements arranged in a straight line in parallel with the bottom of said receptacle.

8. An ultrasonic diagnosing apparatus according to claim 1, wherein said membrane is transparent to visible light.

* * * * *